US009631616B2

(12) United States Patent
Trump et al.

(10) Patent No.: US 9,631,616 B2
(45) Date of Patent: Apr. 25, 2017

(54) DEVICE AND METHOD FOR UPTAKE OR RELEASE OF A LIQUID

(71) Applicant: STRATEC Biomedical AG, Birkenfeld (DE)

(72) Inventors: Martin Trump, Birkenfeld (DE); Tibor Horvath, Birkenfeld (DE)

(73) Assignee: STRATEC Biomedical AG, Birkenfeld (DE)

( * ) Notice: Subject to any disclaimer, the term of this patent is extended or adjusted under 35 U.S.C. 154(b) by 108 days.

(21) Appl. No.: 13/933,403

(22) Filed: Jul. 2, 2013

(65) Prior Publication Data

US 2014/0010667 A1 Jan. 9, 2014

(51) Int. Cl.
*B01L 3/02* (2006.01)
*F04B 49/00* (2006.01)
*G01N 35/10* (2006.01)

(52) U.S. Cl.
CPC .......... *F04B 49/002* (2013.01); *B01L 3/0217* (2013.01); *G01N 35/1016* (2013.01); *B01L 2200/146* (2013.01); *B01L 2200/147* (2013.01); *B01L 2200/148* (2013.01)

(58) Field of Classification Search
CPC ...... B01L 3/02; B01L 3/0237; B01L 2200/06; B01L 2200/0605; B01L 2200/14; B01L 2200/143; B01L 2200/146
USPC .......................... 436/180; 422/501, 509, 521; 73/864.01–864.25
See application file for complete search history.

(56) References Cited

U.S. PATENT DOCUMENTS

| 4,675,301 | A | 6/1987 | Charneski | |
|---|---|---|---|---|
| 6,370,942 | B1 | 4/2002 | Dunfee | |
| 2001/0014477 | A1* | 8/2001 | Pelc | B01L 3/0265 222/422 |
| 2006/0090576 | A1 | 5/2006 | Sander | |
| 2006/0127238 | A1 | 6/2006 | Mosier | |
| 2007/0059215 | A1 | 3/2007 | Huang | |
| 2008/0196762 | A1 | 8/2008 | Mallett | |
| 2012/0090704 | A1 | 4/2012 | Laverdiere | |
| 2014/0138405 | A1* | 5/2014 | Inoue | 222/55 |

FOREIGN PATENT DOCUMENTS

| EP | 1 412 759 | | 4/2004 |
|---|---|---|---|
| EP | 2009 449 | A1 | 12/2008 |
| WO | 0188549 | A1 | 11/2001 |
| WO | 02073215 | | 9/2002 |

\* cited by examiner

*Primary Examiner* — Jan Ludlow
(74) *Attorney, Agent, or Firm* — 24IP Law Group; Timothy R DeWitt

(57) ABSTRACT

A device and a method for dosing an uptake or a release of a liquid. The device comprises a pump pumping a fluid, a pump drive driving the pump, and a fluid channel connected to the pump. A tip is connected to the fluid channel comprising an opening for the uptake or the release of the liquid. At least one flow sensor measures a flow rate of the fluid in the fluid channel. A controller monitors and adjusts the flow rate and/or pressure in the fluid channel.

9 Claims, 8 Drawing Sheets

DEVICE AND METHOD FOR UPTAKE OR RELEASE OF A LIQUID

CROSS-REFERENCE TO RELATED APPLICATIONS

This application claims benefit to and priority of UK Patent Application No. 1212155.4 filed on 9 Jul. 2012 and UK Patent Application No. 1310516.8 by the same inventor and having the same title.

BACKGROUND OF THE INVENTION

Field of the Invention

The field of the invention relates to a device and a method for uptake or release of a liquid.

Brief Description of the Related Art

Automated analyser systems for use in clinical diagnostics and life sciences are produced by a number of companies. For example, the Stratec Biomedical AG, Birkenfeld, Germany, produces a number of devices for specimen handling and detection for use in automated analyser systems and other laboratory instrumentation.

European Patent No. 1412759 B1 discloses a method for evaluating a liquid dosing process in a container, which is at least partially filled with a gas. According to the disclosed method, a temporal course of at least one state variable p of a medium contained in said container is determined essentially over the entire duration of the dosing process. The temporal course of the at least one state variable p is graphically or mathematically compared with a pre-determined state variable nominal range by means of a correlation method, and an evaluation result is obtained according to the results of the comparison.

U.S. Pat. No. 6,370,942 B1 describes liquid aspiration method, which includes a method for determining the quality of the aspirated sample through mathematical analysis of the pressure profile generated before, during, and after the aspiration process and comparison of the results with pre-determined known values. The mathematical analysis is based on methods of numerical calculus.

European Patent No. 2009449 A1 discloses a method for controlling a pipetting process by calibrating a set of process variables applied during the pipetting. The calibrating is based on measuring a pressure time characteristic during dosing a liquid to be dosed using a reference set of process variables.

U.S. Patent Application Publication No. 2008/0196762 A1 discloses a system for delivering flow materials at constant flow rates by adjusting a pump and a flow regulator based on flow rate data delivered by a pressure sensor.

U.S. Patent Application Publication No. 2006/0090576 A1 discloses a method and an apparatus for dosing volumes of a liquid. The apparatus comprises a sensor for measuring a pressure inside a gas displacement system and a control unit for actuating a drive to displace the gas in the gas displacement system. The volume of liquid is determined by calculating a product of a measured pressure and an apparatus parameter.

U.S. Pat. No. 4,675,301 discloses a dispensing apparatus for providing more accurate volume of dispensed liquid by controlling a pressurizing means within the dispensing container. A control system determines the difference of a stored signal and a sensed signal corresponding to a pressure within a container partially filled with the liquid, and produces a negative or a positive pressure difference if the absolute value of the determined difference exceeds a tolerance factor.

U.S. Patent Application Publication No. 2006/0127238 A1 discloses an apparatus for fluid flow control and metering. The apparatus comprises a flow sensing means and a controller to control output of a hydraulic fluid pressure means in order to maintain a constant differential pressure at the outlet of the flow sensing means and to provide nanoliter accuracy of microliter volumes.

U.S. Patent Application Publication No. 2007/0059215 A1 discloses a micro pipette sensing device comprising a micro pipette and a sensing device. The sensing device senses correct gas flow, gas displacement, or gas flow variation caused by leakage or mechanical clearance. An information receiving apparatus receives information from the sensing device in order to control the volume aspirated by feeding back information to the micro pipette.

U.S. Patent Application Publication No. 2012/0090704 A1 discloses a liquid flow controller and a precision dispense apparatus for controlling the flow rate of a fluid to be at a certain rate. The liquid flow controller comprises a fluid control valve between an inlet and an outlet of which a pressure drop is measured and converted into a flow rate of the controlled fluid. The measured flow rate is sent to a controller which modulated one or more valves to obtain a desired flow rate.

It is an object of the present invention to provide an alternative device and a method for dosing the uptake or the release of a liquid.

SUMMARY OF THE INVENTION

The present disclosure relates to a device for uptake or release of a liquid. The device comprises a pump pumping a fluid, a pump drive driving the pump, and a fluid channel connected to the pump. A tip is connected to the fluid channel comprising an opening for the uptake or the release of the liquid. At least one flow sensor measures a flow rate of the fluid in the fluid channel. A controller monitors and adjusts the flow rate in the fluid channel.

The flow sensor may be suitable for measuring the flow rate unidirectionally or bidirectionally.

The tip may be a pipette, or the tip may be attachable.

The liquid may be one of cerebrospinal fluid, blood, urine, sputum, mucus, and saliva, or a component thereof.

The present disclosure further relates to a method for dosing an uptake or a release of a liquid. The method comprises the steps of pumping a fluid with a pump connected to a fluid channel, measuring a time course of a flow rate and/or the pressure of the fluid in the fluid channel with a flow sensor during the pumping of the fluid, monitoring and adjusting the flow rate and/or the pressure in the fluid channel and thereby controlling the uptake or the release of the liquid in a tip connected to the fluid channel.

The monitoring of the time course of the flow rate and/or the pressure may comprise calculating a plurality of time intervals within the time course of the flow rate data.

The monitoring of the time course of the flow rate and/or the pressure may comprise calculating a first time interval beginning with the activating of the pump and ending when the flow rate passes a threshold value.

The monitoring of the time course of the flow rate and/or the pressure may comprise calculating a second time interval beginning with the deactivating of the pump and ending when flow rate passes a threshold value.

The monitoring of the time course of the flow rate and/or the pressure may comprise calculating a third time interval beginning with the output power of the pump being substantially zero and ending with the flow rate being substantially zero.

The monitoring of the time course of the flow rate and/or the pressure may comprise calculating a first rate of change of the flow rate between the end of the first time interval and the output power of the pump reaching a maximum value.

The monitoring of the time course of the flow rate and/or the pressure may comprise calculating a second rate of change of the flow rate between the end of the second time interval and the output power of the pump being zero.

The monitoring of the time course of the flow rate and/or the pressure may comprise monitoring whether the flow rate is within a flow rate range of tolerance and/or the pressure is within a pressure range of tolerance during a fourth time interval beginning at a predefined moment and ending when the deactivating of the pump begins.

The monitoring of the time course of the flow rate and/or the pressure may comprise calculating a standard deviation of the flow rate and/or pressure, and/or monitoring whether the flow rate is within a flow rate range of tolerance and/or the pressure is within a pressure range of tolerance during a predefined time interval.

The disclosure further relates to a use of the device for monitoring the uptake or the release of the liquid.

The device may be used in a therapeutic, diagnostic or analytic system.

DETAILED DESCRIPTION OF THE INVENTION AND THE FIGURES

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

Figure 1:
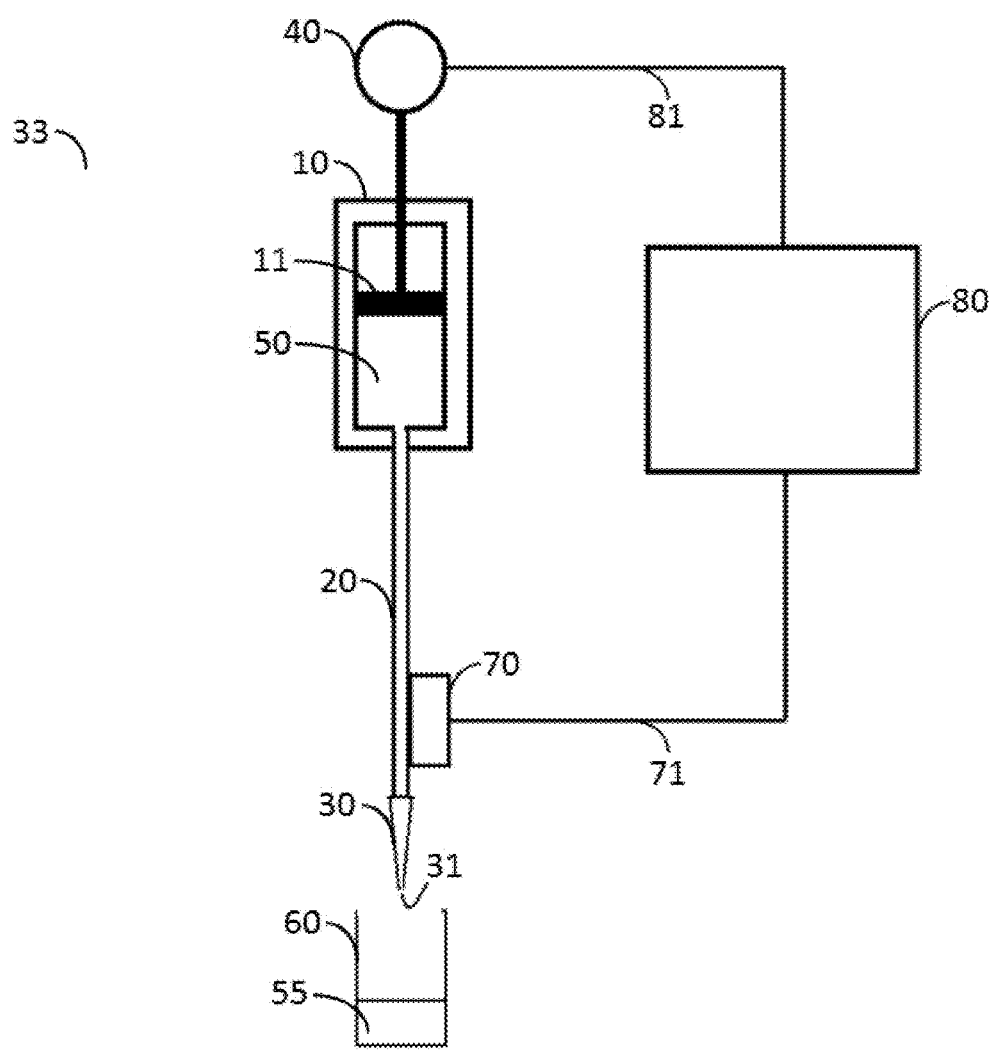
FIG. 1 shows a scheme of a device according to the invention.

As shown in FIG. 1, the device 33 comprises a pump 10, a hollow passage 20 connected to the pump 10, and a tip 30 connected to the hollow passage 20. The pump 10 comprises a piston 11 that is moved by a pump drive 40 such that it pumps a fluid 50. The tip 30 may be attachable or may be fixed to the hollow passage 20. The fluid 50 may flow in a space comprised among a pump chamber of the pump 10, the hollow passage 20 and the tip 30. The term fluid channel is to be understood to mean part or whole of the space.

The pump 10 may pump the fluid 50 towards the tip 30 by exerting an excess of pressure on the fluid 50 by moving the piston 11 towards the tip 30 in FIG. 1. The pump 10 may pump the fluid 50 away from the tip 30 by producing a vacuum by moving the piston 11 away from the tip 30 in FIG. 1.

The tip 30 may comprise the fluid 50.

Equally, the tip 30 may comprise a liquid 55. If the tip 30 comprises the liquid 55, then by pumping the fluid 50 towards the tip 30 in FIG. 1 the liquid 55 would be released from the tip 30. In one aspect of the disclosure, the liquid 55 would be released into a container 60. The container 60 may be a sample carrier or a storage container.

If the tip 30 comprises the liquid 55 and an opening 31 of the tip 30 is surrounded by the liquid 55, then pumping the fluid 50 away from the tip 30 in FIG. 1 the tip 30 would take up more liquid 55.

It is conceivable that the liquid 55 is a body liquid provided to a diagnostic laboratory or automated analyser system as a sample that was previously excreted, extracted, or isolated. The body liquid may be selected from the group comprising cerebrospinal fluid, blood, urine, sputum, mucus, and saliva, or a component of any of the body fluids.

The device 33 comprises sensor unit 70 comprising a flow sensor for measuring a flow rate of the fluid 50 through the hollow passage 20. Flow sensors are known that measure a flow rate in a single direction or in two opposite directions. A flow sensor measuring a flow rate in two opposite directions assigns a positive sign to one of the two directions and a negative sign to the other direction.

The flow rate measured by the flow sensor corresponds to a change of volume of the fluid 50 that is, by the laws of Thermodynamics, directly linked to changes in pressure and temperature of fluid 50 contained in the pump 10 and the hollow passage 20. This is, for instance, expressed by the ideal gas law. Changes in state variables, as the changes in volume, temperature or pressure just mentioned, are linked to each another by the Maxwell relations. In the device 33 according to the present invention, the temperature of the fluid 50 is always known, since a calibration of the flow sensor is based on a measurement of temperature of the fluid 50.

It is an advantage of the present invention to employ the flow sensor. The flow sensor senses small flow rates of the fluid 50 caused by a small pressure change. Such a small pressure change may arise when a pressure difference between the pump chamber of the pump 10 and the opening 31 of the tip 30 suddenly builds up, for example when the opening 31 of the tip 30 comes into contact with the liquid 55. The small pressure change also arises if the tip 30 is partially filled.

Figure 2:
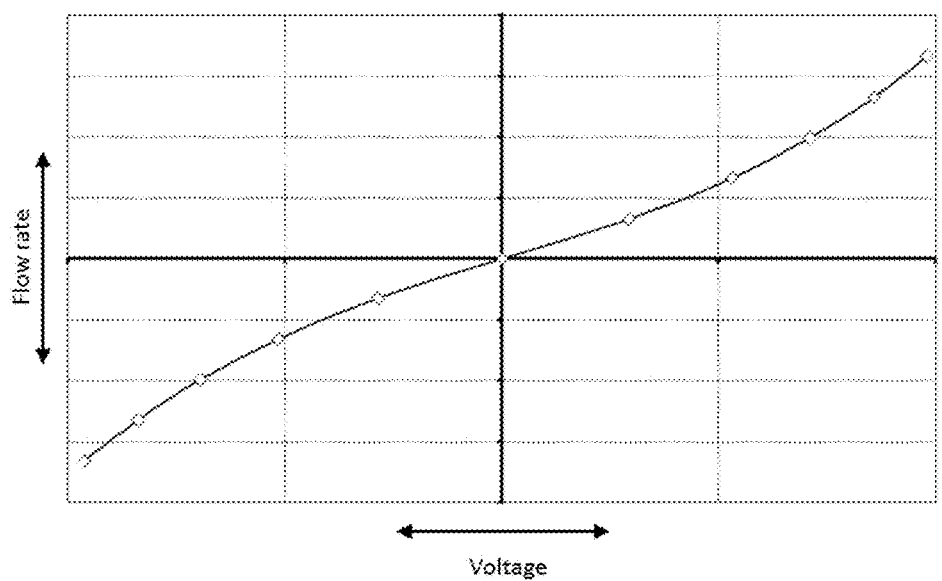
FIG. 2 shows a calibration curve for the flow sensor.

The flow sensor senses a signal according to the quantity and direction of the flow rate and outputs flow rate data 71 after transforming the signal. The flow rate data 71 is one possible type of sensor data 71. The flow sensor transmits the flow rate data 71 to a controller 80. The controller 80 transforms the signal with the help of a calibration curve, i.e. formula, or a calibration table. FIG. 2 shows a calibration curve of for the flow sensor. The calibration curve is a mapping from flow rates to voltages permitting to assign a flow rate to a given voltage.

A calibration of the flow sensor can easily be done, e.g. before and after a measurement, in order to evade possible measurement errors. The calibration may be done during cleaning of the hollow passage 20 or an initialising of the pump drive 40.

In one aspect of the invention, the sensor unit 70 also comprises a pressure sensor for measuring a pressure in a pump chamber of the pump 10 or in the hollow passage 20. Pressure data output by the pressure sensor is another possible type of sensor data 71.

The controller 80 monitors the flow rate data 71 and the pressure data 71. It is conceivable that the controller 80 further controls sensors measuring a position or a temperature. The controller 80 further records time courses of the flow rate data 71, processes time courses of flow rate data 71, records parameters for controlling the pump drive 40 and for processing time courses of the flow rate data 71 for an uptake or a release of different liquids and for different tips, records calibration curves, calibration formulas or calibration tables, and comprises means for processing data from other sensors.

The controller 80 transmits a control signal 81 to the pump drive 40 indicating whether an output power of the pump drive 40 should be increased, decreased, or remain constant.

Figure 3:
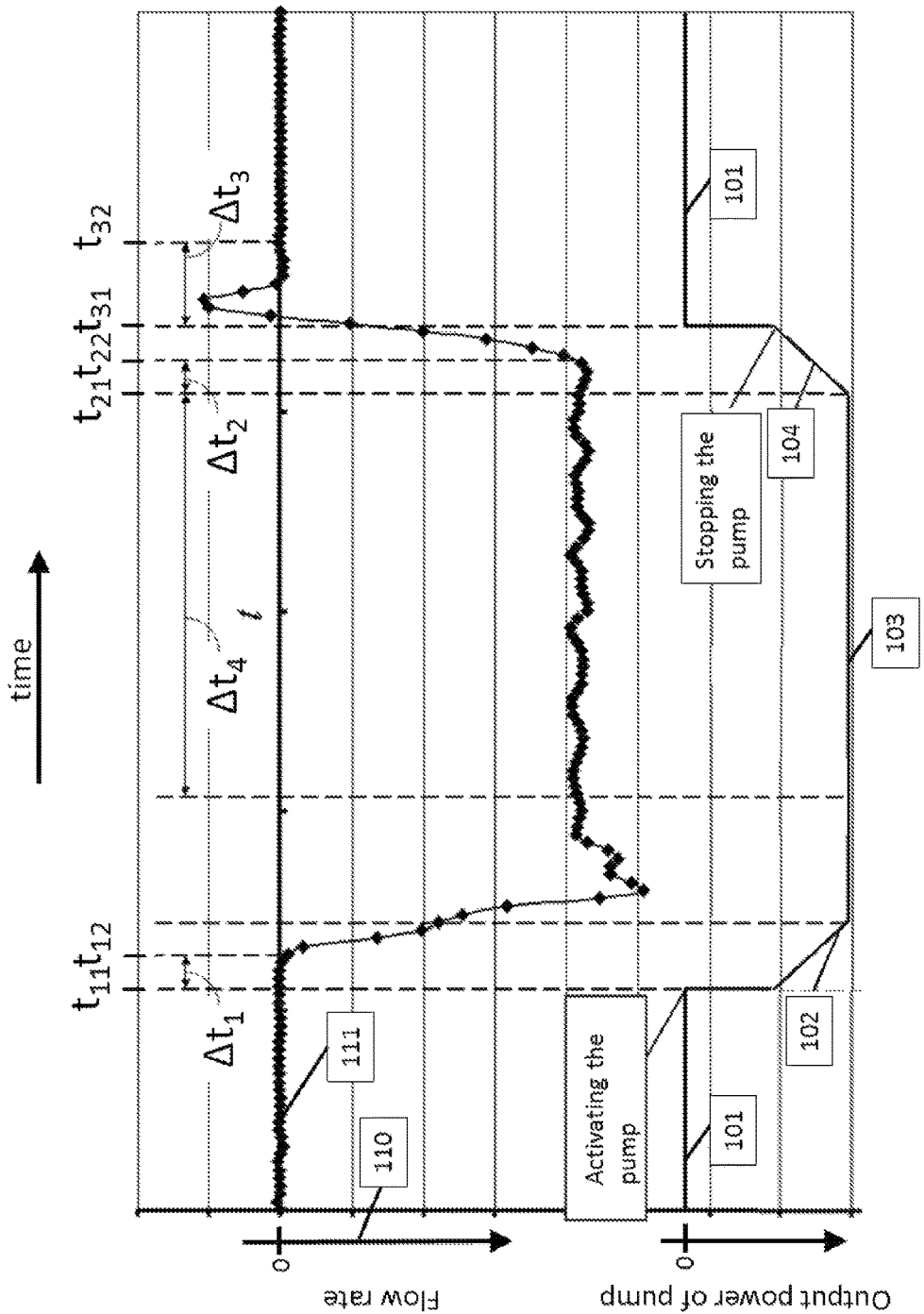
FIG. 3 shows a the output power of the pump and a time series of flow rate data during an uptake or a release of a liquid.

A time course 111 of the flow rate data 71 shown in FIG. 3 represents the flow rate data 71 measured by the flow sensor during the uptake or the release of the liquid 55. The time course 111 entirely covers the uptake or the release of the liquid 55. According to the sign of the axis 110, the flow rate data 71 of the time course 111 represents the uptake or the release of the liquid 55.

In one aspect of the disclosure, the controller 80 monitors the time course 111 of the flow rate data 71 in order to calculate quality measures of the uptake or the release of the liquid 55. The controller 80 calculates a plurality of time intervals $\Delta t_1$, $\Delta t_2$, and $\Delta t_3$, as shown in FIG. 3, and a plurality of properties of the time course 111 of the flow rate data 71 during the uptake or the release of the liquid 55. The time intervals $\Delta t_1$, $\Delta t_2$, and $\Delta t_3$ and the plurality of properties of the time course 111 for both the uptake or the release of the liquid 55 can be described in the same terms. When amounts of flow rate are compared, it is useful to employ the mathematical notion of the absolute value, thereby avoiding the sign assigned to the flow rate data 71 representing the direction of the flow, i.e. the uptake or the release of the liquid 55. The absolute value of a real number equals the real number if the real number is positive, and equals the negative of the real number if the real number is negative.

The controller 80 calculates a first time interval $\Delta t_1$. The controller 80 sends the control signal 81 to the pump drive 40 activating the pump drive 40 during an activation phase beginning at a time $t_{11}$. The pump drive 40 accelerates the pump 10 through an acceleration ramp 102 (see FIG. 3) to a maximum value 103 of the output power of the pump 10. The change of the output power of the pump 10 during the acceleration 102 results in a change of the flow rate data 71. The flow rate data 71 passes through a first threshold value at a time $t_{12}$. The first time interval $\Delta t_1$ then equals a difference of the time $t_{12}$ and the time $t_{11}$.

The controller 80 calculates a second time interval $\Delta t_2$. The controller 80 sends the control signal 81 to the pump drive 40 deactivating the pump drive 40 during a deactivation phase beginning at a time $t_{21}$. The pump drive 40 decelerates the pump 10 through a deceleration ramp 104 (see FIG. 3) until the output power decreases to a resting value 101, i.e. a value of substantially zero output power. The change of the output power of the pump 10 during the deceleration 104 results in a change of the flow rate data 71. The flow rate data 71 passes through a second threshold value at a time $t_{22}$. The first time interval $\Delta t_2$ then equals a difference of the time $t_{22}$ and the time $t_{21}$.

The controller 80 calculates a third time interval $\Delta t_3$ after ending the uptake or the release of the liquid 55. The third time interval $\Delta t_3$ begins with the output power of the pump 10 equalling the resting value 101 at a time $t_{31}$ and the ends with the flow rate data 71 being substantially zero at a time $t_{32}$. The first time interval $\Delta t_3$ then equals a difference of the time $t_{32}$ and the time $t_{31}$.

The controller 80 calculates a first rate of change of the flow rate data 71 during a time interval beginning at the end of the first time interval $\Delta t_1$ and ending when the output power of the pump 10 reaches the maximum value 103. The first rate of change of the flow rate data 71 is calculated during the acceleration ramp 102, i.e. when the output power of the pump 10 is being increased.

The controller 80 calculates a second rate of change of the flow rate data 71 during a time interval beginning at the beginning of the second time interval $\Delta t_2$ and ending when the output power of the pump 10 reaches the resting value 101. The second rate of change of the flow rate data 71 is calculated during the deceleration ramp 104, i.e. when the output power of the pump 10 is being decreased.

During a fourth time interval $\Delta t_4$ the controller 80 calculates a degree of constancy of the flow rate data 71. The fourth time interval $\Delta t_4$ begins at a predefined time $t_{41}$ and ends at the beginning of the deceleration ramp 104 at the time $t_{21}$. During the fourth interval the output power of the pump 10 is at the maximum value 103. The controller 80 monitors whether the flow rate data 71 is within a flow rate range of tolerance during the fourth time interval $\Delta t_4$, and calculates the degree of constancy.

In one aspect of the invention, the controller 80 further monitors whether the pressure data 71 is within a pressure range of tolerance during the fourth time interval $\Delta t_4$. In a further aspect of the invention, The monitoring of the time course of the flow rate and/or the pressure may comprise monitoring whether the flow rate is within a flow rate range of tolerance and/or the pressure is within a pressure range of tolerance during a predefined time interval.

After the uptake or the release of the liquid 55, i.e. after the output power of the pump 10 has reached the resting value 101, the controller 80 calculates a standard deviation of the flow rate data 71.

In what follows, situations potentially occurring during the uptake or the release of the liquid 55 and affecting the quality thereof are described.

Figure 4:
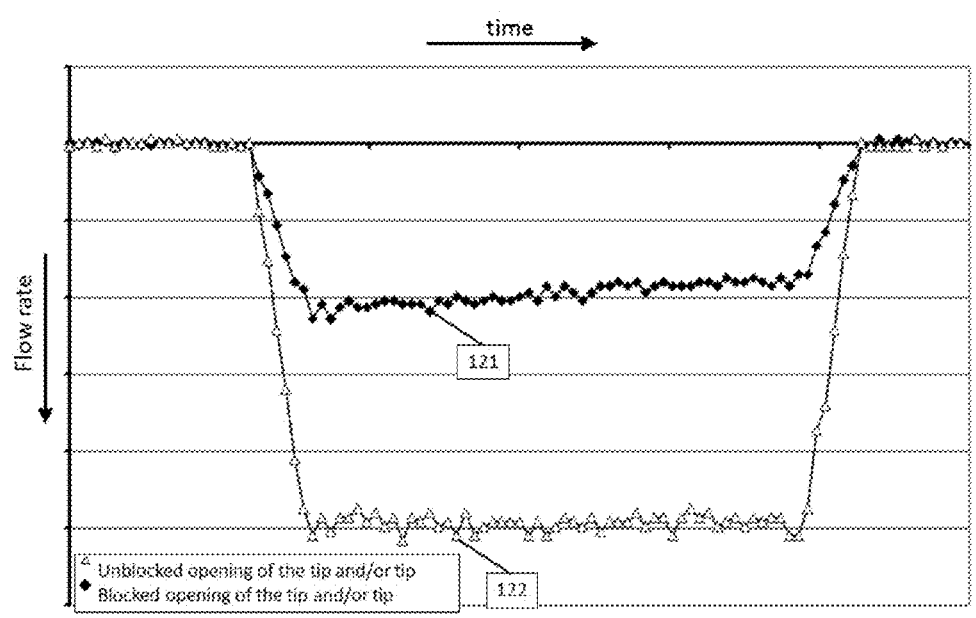
FIG. 4 shows a comparison of two time series of flow rate data during an uptake or release of a liquid, one with a blocked opening of the tip and/or tip, the other unblocked.

It is conceivable that the uptake or the release of the liquid 55 may be obstructed. Fibrin fibers or coagulated blood cells or particles might block the opening 31 of the tip and/or the tip 30 and thereby obstruct the uptake or release of the liquid 55. FIG. 4 shows a time course 121 of the flow rate data 71 (indicated by the filled diamonds) during the uptake or the of the liquid 55 with the opening 31 of tip 30 and/or the tip 30 being blocked. For comparison a time course 122 of the flow rate data 71 (indicated by the unfilled triangles) during the uptake of the liquid 55 is shown when the opening 31 of the tip and/or the tip 30 is unblocked.

The obstruction of the uptake of the liquid 55 affects the time course 122 of the flow rate data 71. The absolute value of the first rate of change of the flow rate data 71 is smaller for the time course 121 than for the time course 122. Furthermore, the absolute value of the flow rate data 71 when the output power of the pump 10 reaches the maximum value 103 (see FIG. 3) is smaller for the time course 121 than for the time course 122. This means the pump 10 pumps less liquid 55 during the uptake or the release of the liquid 55 when the opening 31 of the tip 30 and/or the tip 30 is obstructed. Thus, an advantage of the present disclosure is the capability of the disclosed device and method to detect obstructions of the uptake or the release of the liquid 55.

It is furthermore conceivable that a different fluid different to the liquid 55 surrounds the opening 31 of the tip 30 during the uptake of the liquid 55 and flows into the tip 30. When the storage container 60 is empty or the tip 30 is not lowered enough into the storage container 60 (see FIG. 1) the opening 31 of the tip 30 is surrounded by air resulting in air flowing into the tip 30. Air flowing into the tip 30 results in the first time interval $\Delta t_1$ being shorter. Furthermore, the absolute value of the flow rate data 71 when the output power of the pump 10 reaches the maximum value 103 (see FIG. 3) alters according to the different fluid and increases in the case of air.

An advantage of the present disclosure is the capability of the disclosed device and method to detect during the uptake of the liquid 55 whether a different fluid has entered the tip 30 by measuring altered flow rate data 71, as described above. The viscosity or state of matter of different fluids affects the flow rate data 71. It is thus further possible to discriminate different fluids and liquids with the device as disclosed as well as to detect fluids with different states of matter.

It is likewise conceivable that the pump 10 may not function as intended due to failure of the pump drive 40 or a leakage within the device 33. The malfunctioning of the pump 10 may result in an altered output power of the pump 10. The altered output power of the pump 10 results in both the absolute value of the first rate of change of the flow rate data 71 as well as the flow rate data 71 when the output power of the pump 10 reaches the maximum value 103 (see FIG. 3) being altered.

In the case of the leakage within the device 33 the flow rate data 71 may not be zero after the uptake or the release of the liquid 55 because e.g. air may flow into the device 33 through the leakage. Thus, an advantage of the present disclosure is the capability of detecting a malfunctioning of the pump 10 or a leakage within the device 33.

It is furthermore conceivable that the liquid 55 comprises foam or bubbles comprising a further different fluid different to the liquid 55. This results in the further different fluid and the liquid 55 entering into the tip 30 through the opening 31 in an alternating and erratic fashion. The erratic and alternating fashion of entering the tip 30 results in the flow rate data 71 jumping erratically according to whether the further different fluid or the liquid 55 is entering the tip 30 through the opening 31.

Figure 5:
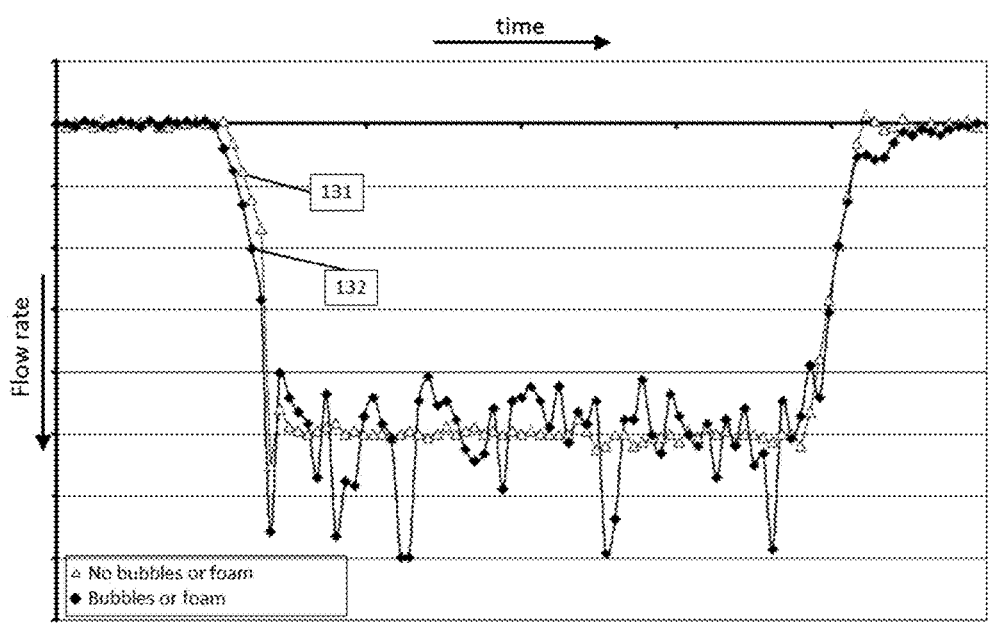
FIG. 5 shows a comparison of two time series of flow rate data during an uptake or release of a liquid, in one case comprising bubbles or foam, in the other case without bubbles or foam.

FIG. 5 shows a time course of the flow rate data 71 during the uptake or release of the liquid 55 when the liquid 55 comprises foam or bubbles. The time course 131 represents the uptake or release of the liquid 55 without foam or bubbles. The time course 132 represents the uptake or release of the liquid 55 with foam or bubbles. Using the same flow rate range of tolerance for both the time course 131 and the time course 132 for calculating the degree of constancy, the time course 132 does not fall within the flow rate range of tolerance if the flow rate range of tolerance is narrow enough. Thus, an advantage of the present disclosure is the capability of detecting whether the liquid 55 comprises foam or bubbles.

Figure 6:
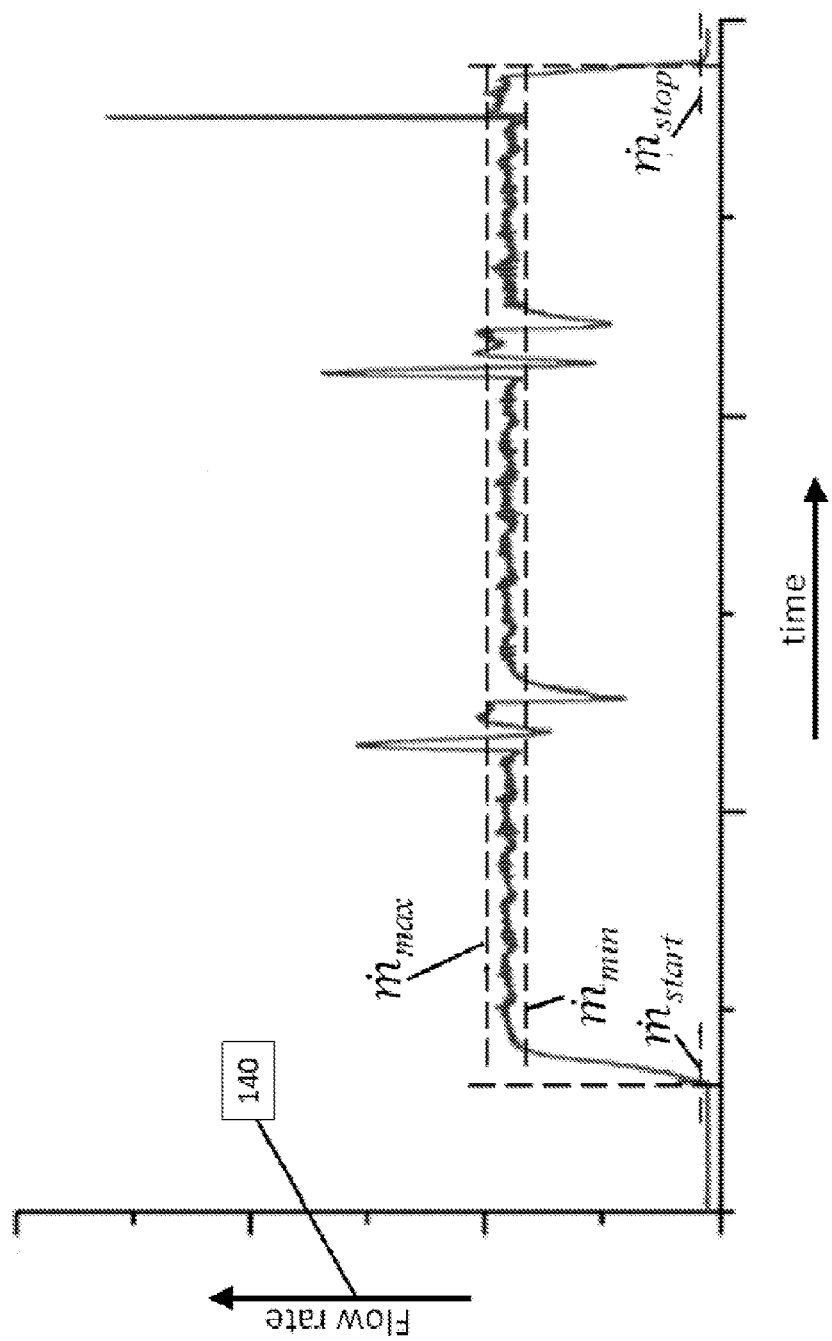
FIG. 6 shows a time series of flow rate data during an uptake or release of a liquid. Three cushions of air separate four parts of the liquid.

By integrating a time course of the flow rate data 71, e.g. the time course 111 in FIG. 3, entirely covering the uptake or the release of the liquid 55, a volume or a mass of the liquid 55 transported during the uptake or the release of the liquid 55 can be calculated with the help of the calibration curve or calibration table. In one aspect of the disclosure, the flow rate data 71 are included in the integration only when the absolute value of the flow rate data 71 is greater than a value $\dot{m}_{start}$ and a value $\dot{m}_{stop}$, and lies in an interval ranging from $\dot{m}_{min}$ to $\dot{m}_{max}$, as shown in FIG. 6. The values $\dot{m}_{start}$ and $\dot{m}_{stop}$, can be estimated from the knowledge of the maximum value of the output power 103 (see FIG. 3) of the pump 10. The values $\dot{m}_{min}$ and $\dot{m}_{max}$ depend on the tip 31 and on the liquid 55. The values from $\dot{m}_{start}$, $\dot{m}_{end}$, $\dot{m}_{min}$, and $\dot{m}_{max}$, have different signs according to whether the uptake or the release of liquid 55 is being integrated.

The calculation of the volume or the mass offers a further way of monitoring the quality of the uptake or the release of the liquid 55. It is possible to calculate the mass or the volume also when several different liquids, separated within the tip 30 and/or the hollow passage 20 from one another by air, are taken up by the device 33 and subsequently released.

FIG. 6 shows the uptake or release of the liquid 55, depending on the sign of the axis 140, wherein three cushions of air separate four parts of the liquid 55. The peaks in the time course of the flow rate data 71 in FIG. 6 are due to the air cushions. The interval ranging from $\dot{m}_{min}$ to $\dot{m}_{max}$ determines the flow rate data 71 to be integrated.

The result of an integration of a time course, i.e. the calculated mass or volume, is compared with an expected mass or volume. Depending on the pump 10, the tip 30, the liquid 55, and the expected mass or volume the result of the integration is judged as acceptable or not by the controller 80.

Thus an advantage of the present disclosure is the capability of additionally controlling the quality of the uptake or the release of the liquid 55 by monitoring a mass or a volume having entered or left the tip 30. By integrating the flow rate data 71 resulting in the mass or the volume and thereupon comparing the mass or the volume to expected results a further measure of the quality of the uptake or the release of the liquid 55 is calculated. The calculation of the mass or the volume can also be done when a plurality of parts of the liquid 55 are separated by air cushions during the uptake or the release of the liquid 55. The redundancy of calculating the mass or volume as described with the respect to the plurality of time intervals $\Delta t_1$, $\Delta t_2$, and $\Delta t_3$ and the plurality of properties of the time series 110 of the flow rate data 71 is of advantage in automated analyser systems. The reliability of the monitoring of automated analyser systems is increased by the redundancy of quality measures.

It is furthermore conceivable to use the device 33 for detection of a surface of a liquid, i.e. for liquid level detection. Lowering the tip 30 of the device 33 towards the liquid 55 in the storage container 60 (see FIG. 1) results in a jump of the flow rate data 71 when the tip 30 hits the level of the liquid 55 in the storage container 60 (see FIG. 7).

Figure 7:
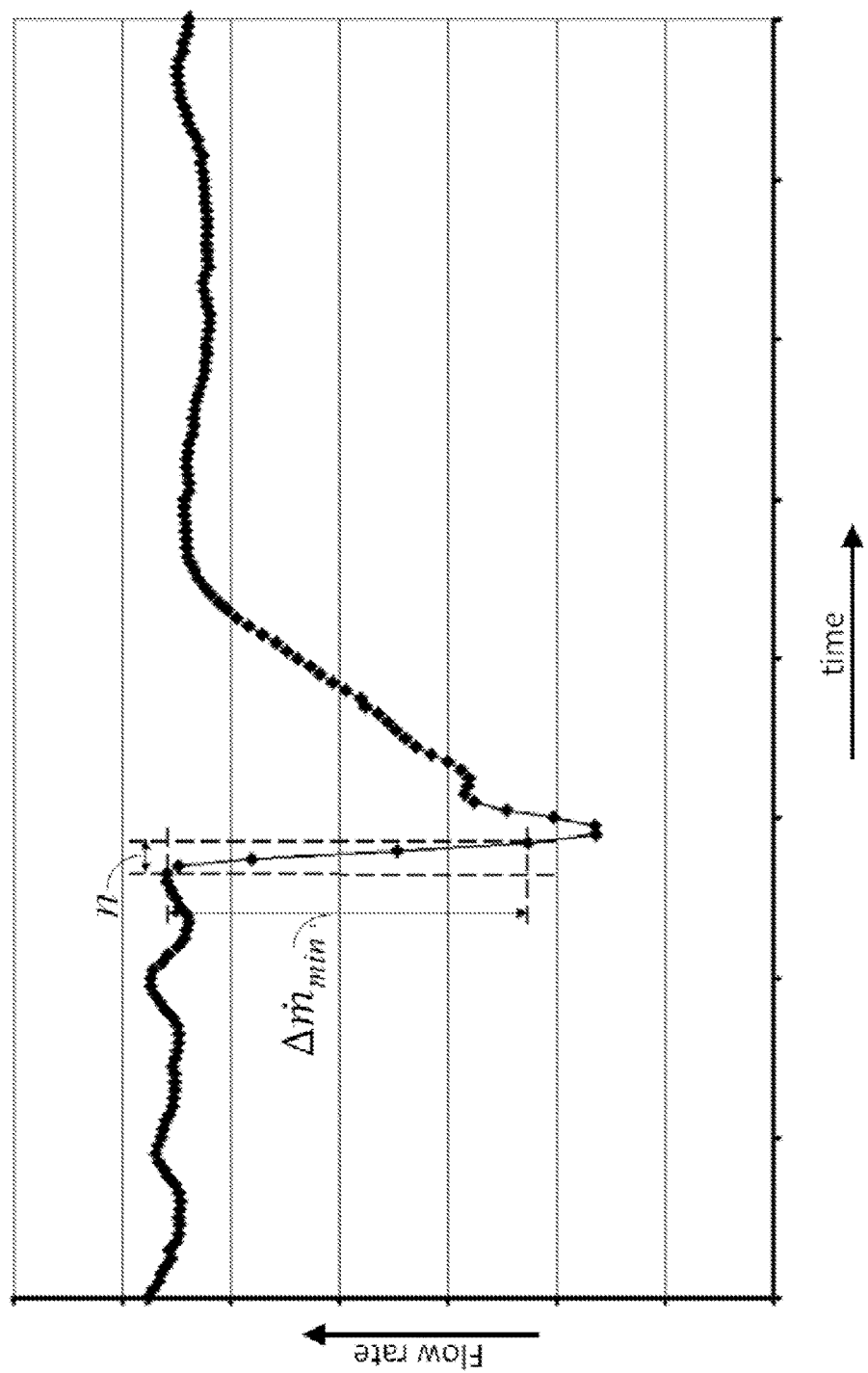
FIG. 7 shows a time series of flow rate data recorded during the detecting of a liquid level while the pump is not running.
Figure 8:
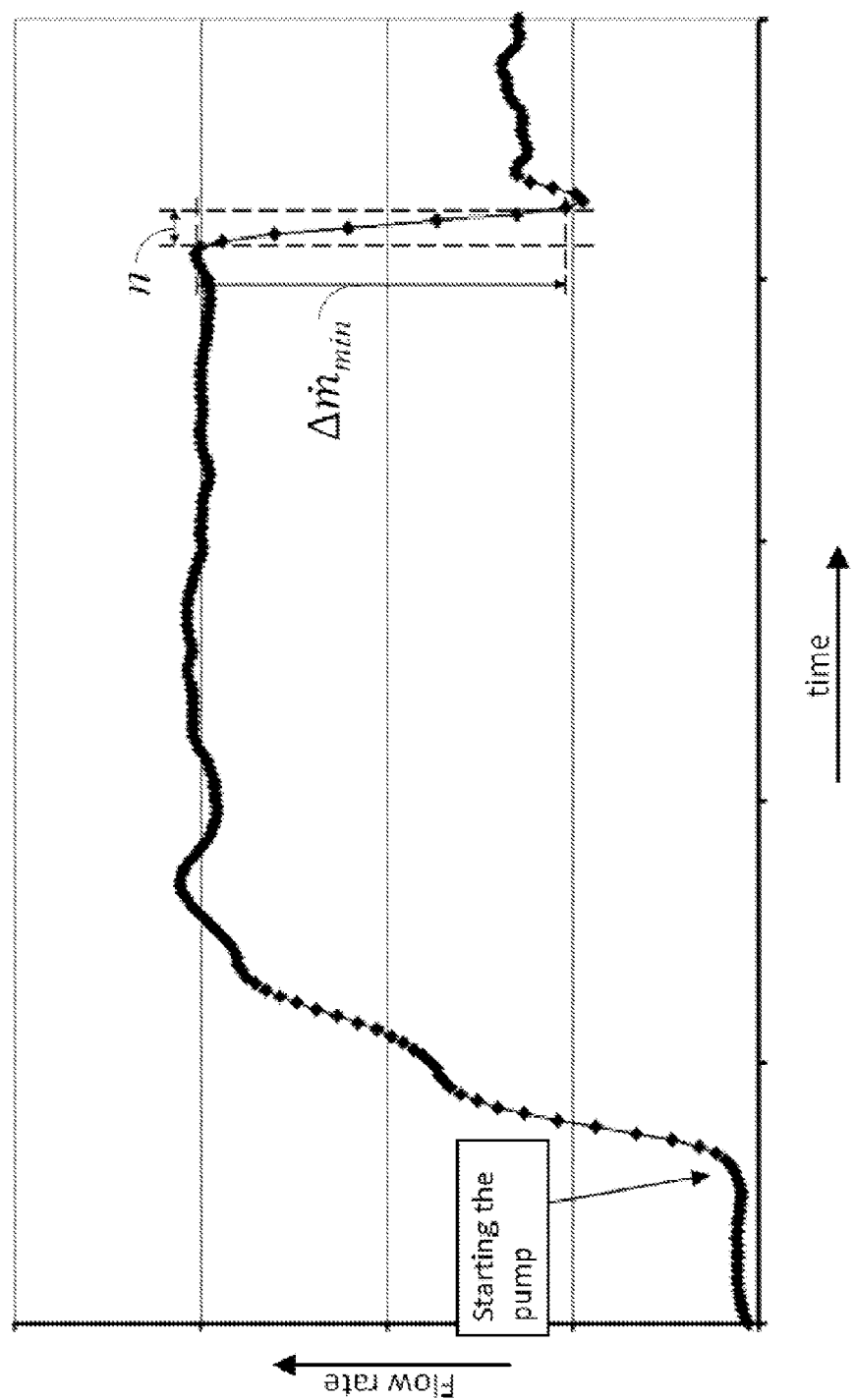
FIG. 8 shows a time series of flow rate data recorded during the detecting of a liquid level while the pump is running.

Depending on the size of the jump of the flow rate data 71 it can be advisable to have the pump 10 running during the lowering of the tip 30 in order to make the jump of the flow rate data 71 more easily detectable. FIG. 7 shows a time course of the flow rate data 71 when the tip 30 is lowered towards the surface of the liquid 55 in the container 60 without the pump 10 running FIG. 8 shows a time course of the flow rate data 71 when the tip 30 is lowered towards the surface of the liquid 55 in the container 60 and the pump 10 is running.

The controller 80 detects a jump in the flow rate data 71 if the jump occurs within a time interval of no more than n multiplied by a sampling time of the flow sensor, and if the jump is larger than a minimum value $\Delta\dot{m}_{min}$. The values of the time interval n and the size of the jump of the flow rate data 71 $\Delta\dot{m}_{min}$ are recorded in the controller 80.

As described above, an advantage of the present disclosure is the capability of detecting liquid levels. Detecting liquid levels prevents a damage of the tip 30 by preventing lowering the tip 30 so far into the storage container 60 that the tip 30 hits the bottom of the storage container 60.

Mathematical methods known from the theory of linear systems, for example numerical transformation, may further be applied to the measured time courses of the flow rate data 71 and/or the pressure data 71. Convoluting and inversely transforming the time course of the flow rate data 71 and/or the pressure data 71 helps in reducing noisiness of the flow rate data 71 and/or the pressure data 71. The aforementioned methods advantageously improve a monitoring and/or a verifying of uptake or release of the liquid 55.

LIST OF REFERENCE NUMBERS

10 Pump
11 Piston
20 Hollow passage
30 Tip
31 Opening of the tip
33 Device
40 Pump drive
50 Fluid
55 Liquid
60 Storage container
70 Sensor unit
71 Sensor data
80 Controller
81 Control signal
101 Resting value of output power
102 Acceleration ramp
103 Maximum value of output power
104 Deceleration ramp
110 Axis of graph
111 Time course of flow rate data
121 Time course of flow rate data
122 Time course of flow rate data
131 Time course of flow rate data
132 Time course of flow rate data
140 Axis of graph

The invention claimed is:

1. A method for dosing an uptake or a release of a liquid, comprising the steps of:
pumping a fluid with a pump connected to a fluid channel;
measuring pressure changes of the fluid in the fluid channel with a flow sensor during the pumping of the fluid for obtaining flow rate data of the fluid;
sending the flow rate data of the fluid to a controller,
calculating with said controller a plurality of time intervals by comparing reserved flow rate data with calibration curves; and
controlling one of the uptake or the release of the fluid in a tip connected to the fluid channel by transmitting a control signal from the controller to a pump drive indicating whether an output power of the pump drive is to be increased, decreased or remain constant, wherein control of the uptake or the release of the fluid in the tip is based at least in part on the calculated time intervals.

2. The method according to claim 1, wherein calculating the plurality of time intervals comprises calculating a first time interval beginning with the activating of the pump and ending when the flow rate passes a threshold value.

3. The method according to claim 2, wherein calculating the plurality of time intervals comprises calculating a second time interval beginning with the deactivating of the pump and ending when the flow rate passes a threshold value.

4. The method according to claim 3, wherein calculating the plurality of time intervals comprises calculating a third time interval beginning with the output power of the pump being substantially zero and ending with the flow rate being substantially zero.

5. The method according to any claim 2, wherein calculating the first time interval comprises calculating a first rate of change of the flow rate between the end of the first time interval and the output power of the pump reaching a maximum value.

6. The method according to claim 3, wherein calculating a second time interval comprises calculating a second rate of change of the flow rate between the end of the second time interval and the output power of the pump being zero.

7. The method according to claim 1, wherein a monitoring and adjusting of at least one the flow rate or pressure in the fluid channel comprises monitoring whether the flow rate is within a flow rate range of tolerance during a fourth time interval beginning at a predefined moment and ending when the deactivating of the pump begins.

8. The method according to claim 1, wherein a measuring of the time course of the pressure comprises monitoring whether the pressure is within a pressure range of tolerance during a fourth time interval beginning at a predefined moment and ending when the deactivating of the pump begins.

9. The method according to claim 1, wherein a monitoring of the time course of one of the flow rate or the pressure comprises calculating a standard deviation of the flow rate during a predefined time interval.

* * * * *